United States Patent
Danaei-Moghaddam (10) Patent No.: US 10,872,212 B2
(45) Date of Patent: Dec. 22, 2020

(54) MICROCHIP DENTURE IMPLANT AND READER SYSTEM AND METHOD

(71) Applicant: Vahid Danaei-Moghaddam, Woodbridge (CA)

(72) Inventor: Vahid Danaei-Moghaddam, Woodbridge (CA)

( * ) Notice: Subject to any disclaimer, the term of this patent is extended or adjusted under 35 U.S.C. 154(b) by 0 days.

(21) Appl. No.: 16/387,511

(22) Filed: Apr. 17, 2019

(65) Prior Publication Data

US 2019/0243997 A1 Aug. 8, 2019

Related U.S. Application Data

(63) Continuation-in-part of application No. 15/807,863, filed on Nov. 9, 2017, now abandoned.

(51) Int. Cl.
| | |
|---|---|
| *G06K 7/10* | (2006.01) |
| *A61C 13/01* | (2006.01) |
| *A61B 5/11* | (2006.01) |
| *A61B 90/98* | (2016.01) |

(52) U.S. Cl.
CPC ........ *G06K 7/10366* (2013.01); *A61B 5/1112* (2013.01); *A61B 90/98* (2016.02); *A61C 13/01* (2013.01); *A61C 2204/005* (2013.01)

(58) Field of Classification Search
CPC ... G06K 7/10366; A61B 90/98; A61B 5/1112; A61C 13/01; A61C 2204/005
See application file for complete search history.

(56) References Cited

U.S. PATENT DOCUMENTS

| | | | | |
|---|---|---|---|---|
| 4,936,775 A | * | 6/1990 | Bennett | C09J 4/00 433/220 |
| 5,760,692 A | | 6/1998 | Block | |
| 6,059,571 A | * | 5/2000 | Kishigami | A61C 13/24 433/167 |
| 6,239,705 B1 | * | 5/2001 | Glen | G08B 21/023 340/572.8 |
| 6,734,795 B2 | | 5/2004 | Price | |
| 7,473,097 B2 | * | 1/2009 | Raby | A61C 13/16 433/24 |
| 8,786,431 B2 | * | 7/2014 | Athalye | H01Q 1/44 340/5.81 |
| 2007/0046461 A1 | | 3/2007 | Radmand | |
| 2009/0237236 A1 | | 9/2009 | Maassarani | |
| 2011/0136076 A1 | | 6/2011 | Li | |

FOREIGN PATENT DOCUMENTS

| | | |
|---|---|---|
| KR | 1020080059699 A | 1/2010 |
| WO | 2017209452 A1 | 12/2017 |

\* cited by examiner

*Primary Examiner* — Seung H Lee
(74) *Attorney, Agent, or Firm* — Argus Intellectual Enterprise; Daniel Enea; Jordan Sworen (57) ABSTRACT

A microchip denture implant and reader system includes a microchip having a transceiver 1150 or transmitter-receiver pair for transmitting a wireless signal containing information relating to a user, and an external reader scanner 130 in communication with the microchip. The microchip mounts in a dental prosthetic item for oral use. The external reader when activated can scan and display or otherwise provide access to the information relating to the user. The microchip and dental prosthetic item, when installed in the mouth of the user, are configured to provide access to the information relating to the user at a given time.

13 Claims, 6 Drawing Sheets

MICROCHIP DENTURE IMPLANT AND READER SYSTEM AND METHOD

CROSS REFERENCE TO RELATED APPLICATION

The present application is a continuation-in-part of copending application Ser. No. 15/807,863 filed Nov. 9, 2017, which is incorporated by reference herein in its entirety.

BACKGROUND OF THE INVENTION

The following includes information that may be useful in understanding the present disclosure. It is not an admission that any of the information provided herein is prior art nor material to the presently described or claimed inventions, nor that any publication or document that is explicitly or implicitly referenced is prior art.

1. FIELD OF THE INVENTION

The present invention generally relates to the field of dentistry and more specifically relates to dental accessories and tracking devices.

2. DESCRIPTION OF RELATED ART

Numerous electronic devices have been introduced to track and locate mobile assets, such as trucks, rail cars, and shipping containers. Hundreds of thousands of these assets have been equipped with tracking and locating transducers. The most sophisticated systems permit location of an asset to within a few feet. Tracking devices, such as radio frequency identification tags (RFID), are increasingly used to mark items to provide a convenient means of determining the location and tracking the movement of the article on which the tag is mounted. Such RFID tags or microchips are also increasingly used to provide identification and location information on people and animals. However, a reliable method of applying and using a microchip has not been created for many items of value or for tracking important items/people of concern. A suitable, affordable, noninvasive solution is desired.

U.S. Pub. No. 2009/0237236 to Sami Maassarani relates to a tooth located GPS person tracking and location method and apparatus. The described tooth located GPS person tracking and location method and apparatus includes an apparatus and method for remotely monitoring the location of a person through a microchip mounted in a tooth of a person which communicates by a communication link to a Global Positioning System to obtain geographic location information relating to the physical location of a person, and by another communication link to a remote tracking device to obtain the geographic information to determine and provide an indication of the physical location of a person. The microchip is disposed in a cavity formed in a tooth of a person which is filled with dental filling material to fix the microchip in the tooth.

BRIEF SUMMARY OF THE INVENTION

Given the foregoing disadvantages inherent in the known dentistry art, the present disclosure provides a novel microchip denture implant and reader system and method. The general purpose of the present disclosure, which will be described subsequently in greater detail, is to provide a personalized, microchip denture implant which will be processed inside part of any type of prosthetics wearable inside a user's mouth and may be accessed by an external reader device.

A microchip denture implant and reader system are disclosed herein. The microchip denture implant and reader system include a microchip including a transceiver 1150 for transmitting a wireless signal and an external reader scanner 130 in communication with the microchip. The wireless signal can contain information relating to a user of dentures or other dental prosthetics. The microchip is adapted to be mounted in a dental prosthetic item to be applied to the mouth of the user. The external reader when activated is configured to scan and provide access to the information relating to the user by displaying it. The microchip and dental prosthetic item, when installed in the mouth of the user, are configured to provide access to the information relating to the user at a given time.

The dental prosthetic item may include a partial denture, orthodontic, dental retainers, or orthopedic appliance, a complete fixed over dental implant supported or complete removable or over implant supported denture. The device may be used to locate, identify or retrieve personal information on a user. The external reader may be used by an authorized third-party-user to scan a cheek portion or mouth of a user and retrieve personal information on the user. The device may be used for a variety of purposes including locating lost or missing people, identifying dead people, retrieving bank information, health history or other important information in emergencies.

The dental lab procedure may include a technician implanting the microchip into a denture or other dental prosthetic item using proper materials. The technician grinds a cavity into a base of the denture or other dental prosthetic item and inserts the microchip within the cavity. Adhesives and acrylic materials may be used to secure and conceal the microchip properly. The dental prosthetic item may then be inserted into the mouth of a user. The information stored on the microchip may then be accessed at a later time by a third-party-user using the external reader scanner 130. The microchip, as manufacture and installed, is protected from damage caused by moisture.

A method of using a microchip denture implant and reader system is also disclosed herein. The method of using the microchip denture implant and reader system may comprise the steps of providing a microchip and an external reader scanner 130; entering and programming the microchip with information relating to a user; preparing a cavity to install the microchip within a dental prosthetic item; installing the microchip within the dental prosthetic item; installing the dental prosthetic item in a mouth of the user; scanning the microchip; and accessing the information relating to the user. The method may further comprise the step of updating the information on the microchip, removing the dental prosthetic item, identifying the user, authorizing a third-party-user. The dental prosthetic item comprises a denture, in some embodiments.

For purposes of summarizing the invention, certain aspects, advantages, and novel features of the invention have been described herein. It is to be understood that not necessarily all such advantages may be achieved by any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a microchip denture implant and reader system and method, constructed and operative according to the teachings of the present disclosure.

The various embodiments of the present invention will from now on be described with the appended drawings, wherein like designations denote like elements.

DETAILED DESCRIPTION

As discussed above, embodiments of the present disclosure relate to dentistry and more particularly to a microchip denture implant and reader system and method as used to improve the use of dental accessories and tracking devices in combination.

Generally speaking, the microchip denture implant and reader system include a customized electronic microchip that may be as small as 5 mm. The microchip may be personalized and inserted into a person's denture (prosthetics or any device a person may wear inside the mouth) and include all desired personal information to be accessed when necessary by an external reader device. Personalized, microchip denture implant will be processed inside part of any type of prosthetics wearable inside person's mouth and will be accessed by an external reader device by tapping or scanning through face (cheek area) or mouth of a person or prosthetic device (denture) itself to access information required.

The device may be used for emergency access of a person's personal information, and preferably the access and installation is agreed to by the host. A quick identification may be made on a lost or abducted person or a dead body. Personal information may include passport, identity, driver's license, social insurance, social security, and accounts. The device can operate in various applications including with patients in emergency rooms, hospitals, or other medical facility; as voter registration; by police and for security clearance; for health history information retrieval (medication, allergy, infective disease, and contact information); to locate lost and abducted seniors, seniors with dementia or Alzheimer's; to help deaf and speechless people; to help people with down syndrome or people needing social assistance; to verify club memberships, bank information, and library access; to pay for grocery shopping; to monitor body temperature and other physical information; and many other applications as suitable. The microchip is customizable and personalized for user needs. Information may be programmed by connecting the microchip to a computer via a chip reader cable, such as a USB-chip reader.

Figure 1:
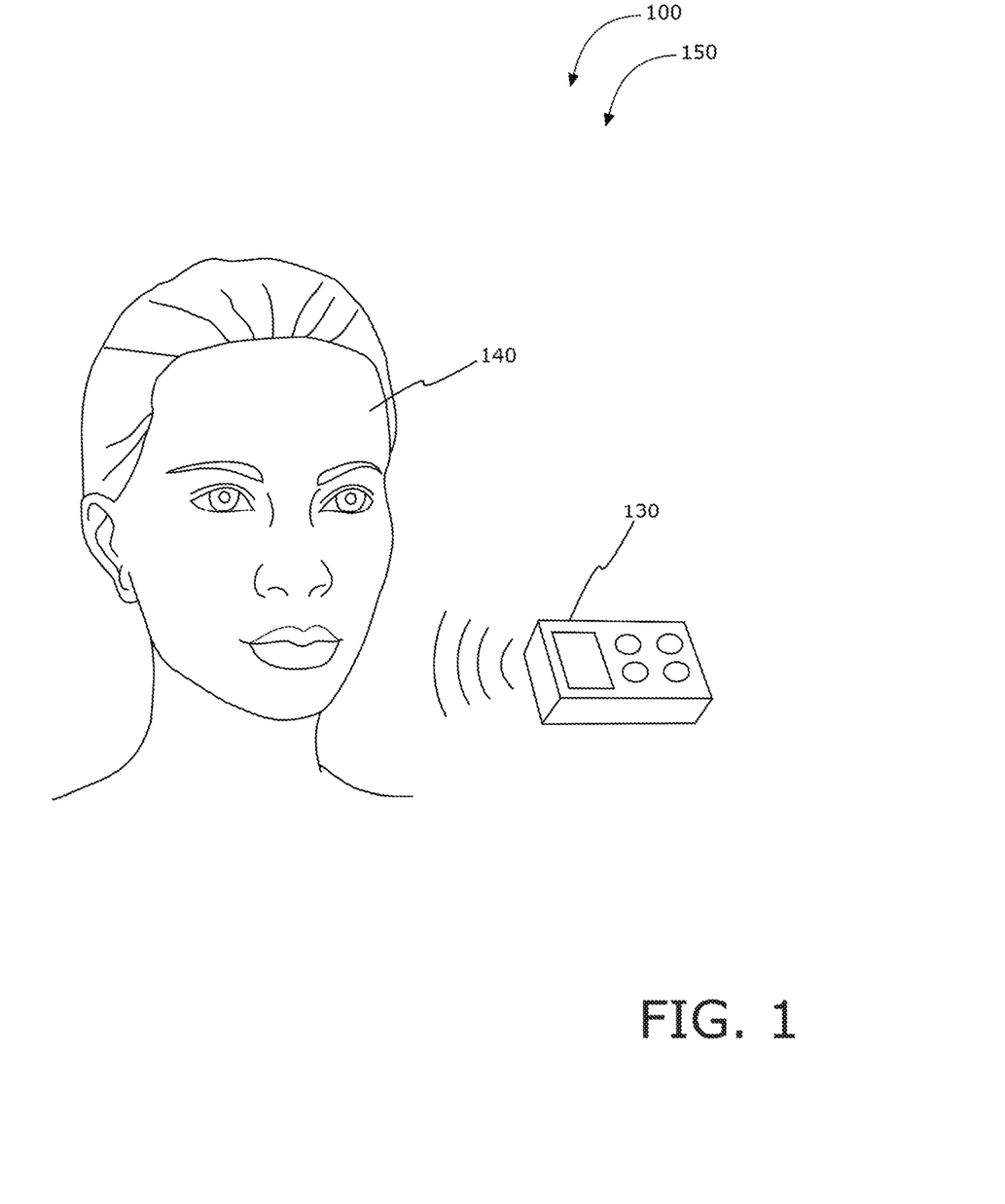
FIG. 1 is a perspective view of the microchip denture implant and reader system during an 'in-use' condition, according to an embodiment of the disclosure.

FIGS. 1-4 show various views of a microchip denture implant and reader system 100. FIG. 1 shows a microchip denture implant and reader system 100 during an 'in-use' condition 150, according to an embodiment of the present disclosure. As illustrated, the microchip denture implant and reader system 100 may include a microchip 110 having a transceiver 1150 for transmitting a wireless signal containing information relating to a user 140, and an external reader scanner 130 in communication with the microchip 110. In some embodiments, the transceiver 1150 can be a separate receiver and transmitter. The microchip 110 mounts in a dental prosthetic item 10 to be applied to a mouth of or worn by the user 140. The external reader 130 when activated is configured to scan and display or otherwise provide access to the information relating to the user 140. The microchip 110 and dental prosthetic item 10 are configured to provide access to information relating to the user 140 at a given time. Sometimes, this information is available to the microchip when the dental prosthetic item 10 is being worn or used by the user 140. In some embodiments, the device is in communication with a global positioning system to obtain geographic location information relating to the physical location of a user 140. In some of these embodiments, the release or communication of geographic location information is strictly under the user's control.

Figure 2:
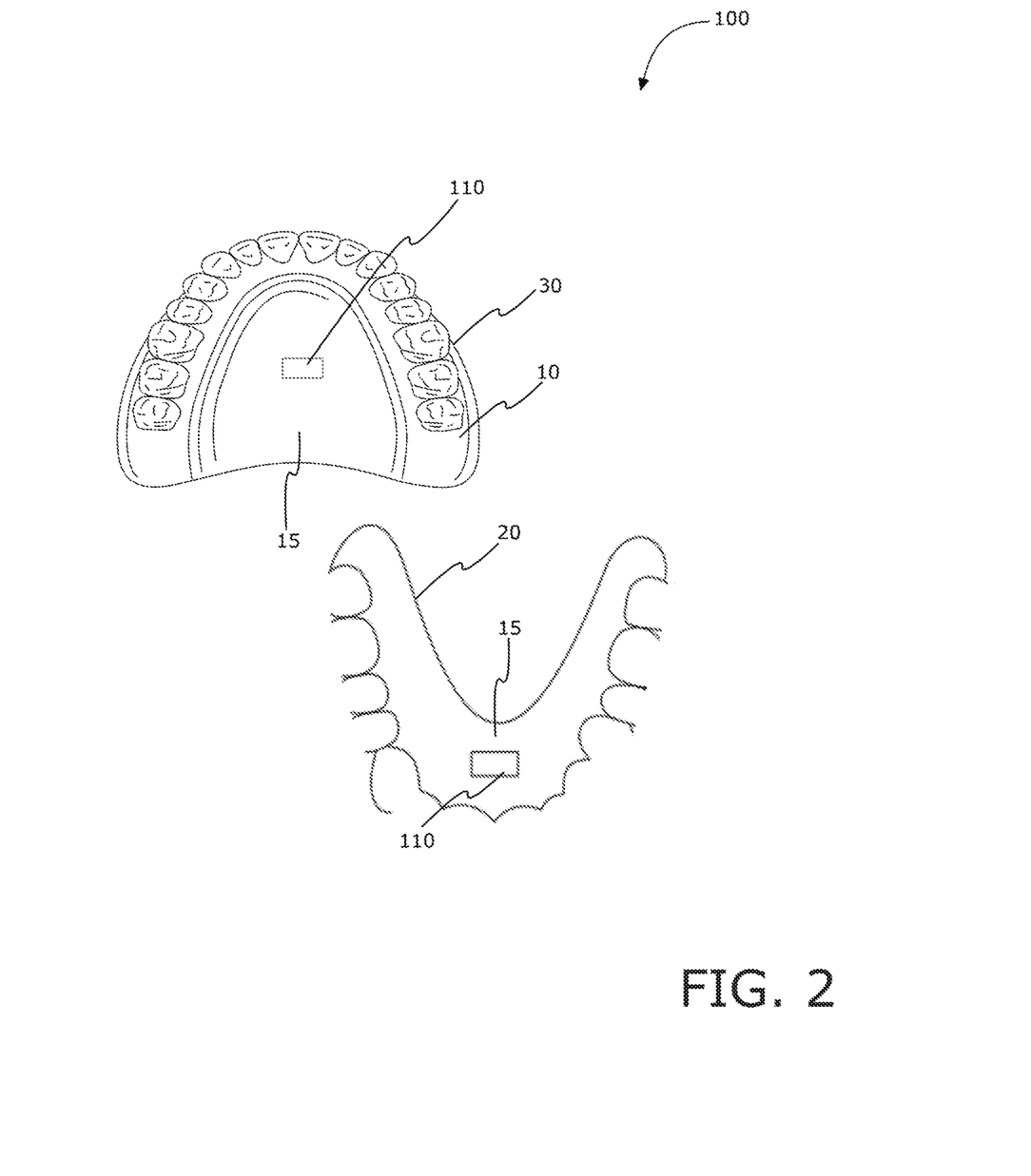
FIG. 2 is a perspective view of the microchip denture implant and reader system of FIG. 1, according to an embodiment of the present disclosure.

Referring now to FIG. 2 showing a perspective view of the microchip denture implant and reader system 100 of FIG. 1, according to an embodiment of the present disclosure. As above, the microchip denture implant and reader system 100 may include the microchip 110 mounted in the user's 140 dental prosthetic item 10. In various embodiments, the dental prosthetic item 10 includes a partial-denture 20, a complete-denture 30, or other suitable orthodontic or orthopedic appliance. The dental prosthetic item 10 is available as a permanent or removable device, dental implant supported or not. The external reader scanner 130 comprises a display and a control panel for third-party-user manipulation. The external reader scanner 130 is portable. The external reader scanner 130 is configured to identify a plurality of different users 140.

Figure 3:
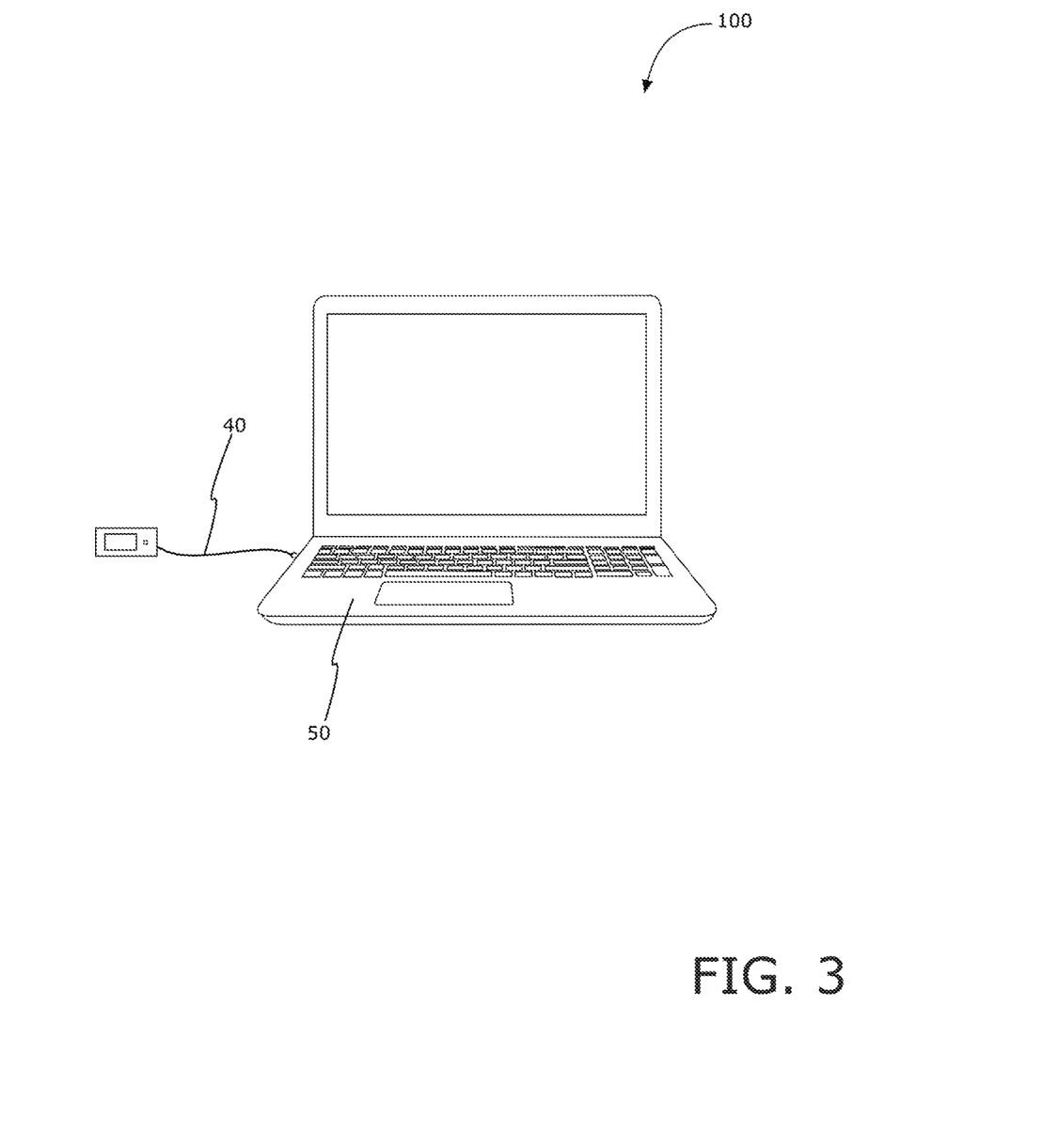
FIG. 3 is a perspective view of the microchip denture implant and reader system of FIG. 1, according to an embodiment of the present disclosure.

FIG. 3 shows a perspective view of the microchip denture implant and reader system 100 of FIG. 1, according to an embodiment of the present disclosure. As above, the microchip denture implant and reader system 100 may include the microchip 110 including the transceiver 1150 for transmitting a wireless signal containing information relating to the user 140, and the external reader scanner 130 is in communication with the microchip 130. The microchip 130 and the transceiver 1150 are configured to operate within the global positioning satellite system for determining the geographical location of the user 140 under the user's control, in some embodiments. In some embodiments, the device provides an intra-oral tracking means useful for locating missing or lost users 140. The microchip 110 is configured to be personalized and store information relating to the user 140.

Figure 4:
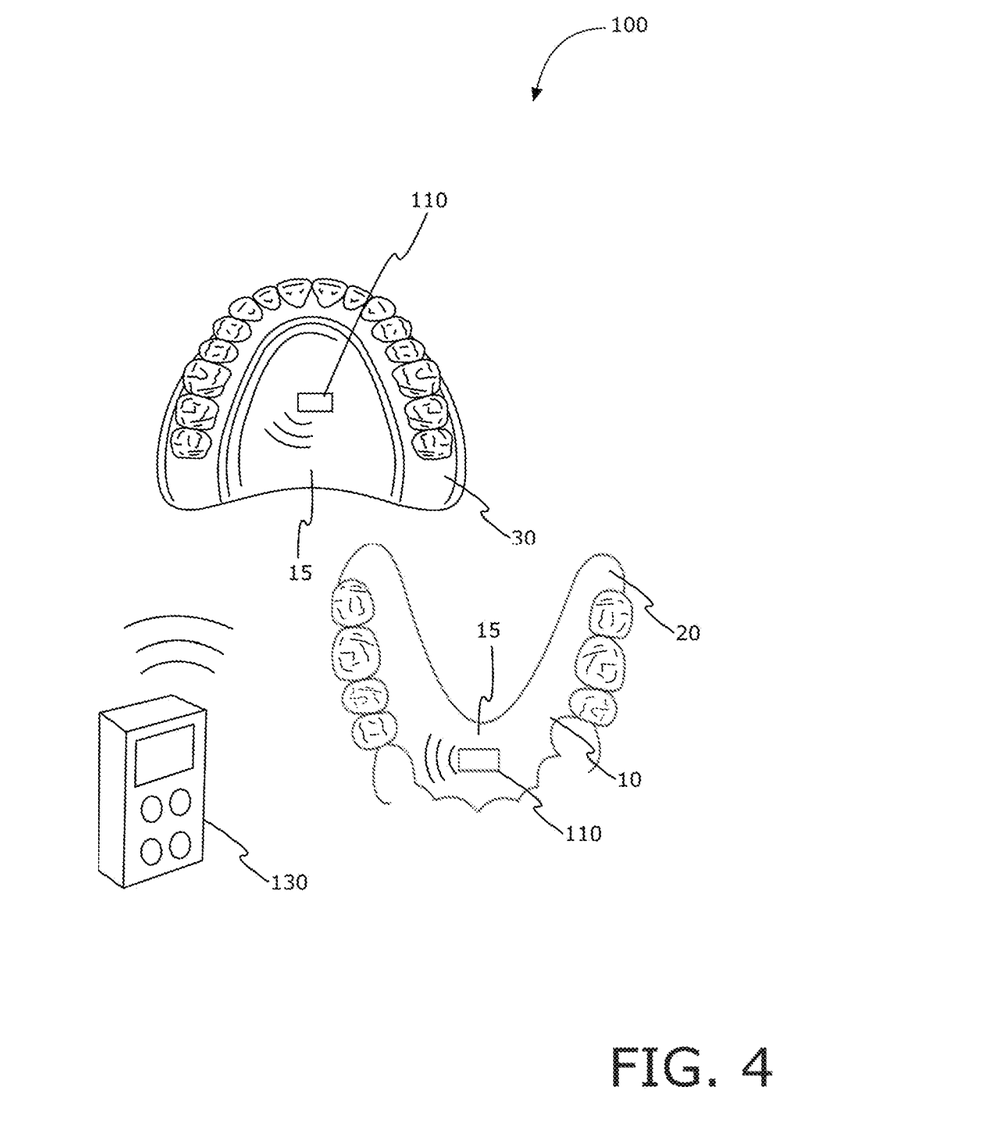
FIG. 4 is a perspective view of the microchip denture implant and reader system of FIG. 1, according to an embodiment of the present disclosure.

Referring now to FIG. 4 showing a perspective view of the microchip denture implant and reader system 100 of FIG. 1, according to an embodiment of the present disclosure. In some embodiments, the dental prosthetic item 10 comprises a base 15. As above, the microchip denture implant and reader system 100 has embodiments that include the microchip 110 mounted on base 15. The microchip 110 has a length and a width of approximately 4 to 6 millimeters. The microchip 110 has functionality for storing personalized information or personalize functionality and for receiving information using a USB chip reader in communication with a computer 50 through a cable 40. The user or third-party user may load the microchip 110 with data and update the data accordingly, as needed.

In some method-based embodiments, a technician takes a dental prosthetic item 10 (necessarily customized to fit the wearer) and modifies the dental prosthetic item 10 to contain the microchip 110. In some embodiments, the modification step has several steps such as milling a space for the microchip 110 in the dental prosthetic item 10. After that, the technician places or inserts the microchip 110 into the milled space and then fixes the microchip 110 in place. In some embodiments, fixing the microchip 110 in place includes gluing or sealing the microchip 110 into the milled space. In some embodiments, the "glue" includes a 2-part resin or a light-activated (e.g., UV) resin or adhesive. Microchip 110 programming can occur before or after placement in the milled space. At any time after programming, the reader 130 can be used to interrogate the microchip 110 either as the dental prosthetic item 10 is worn or after the dental prosthetic item 10 is removed from the user 140.

Figure 6:
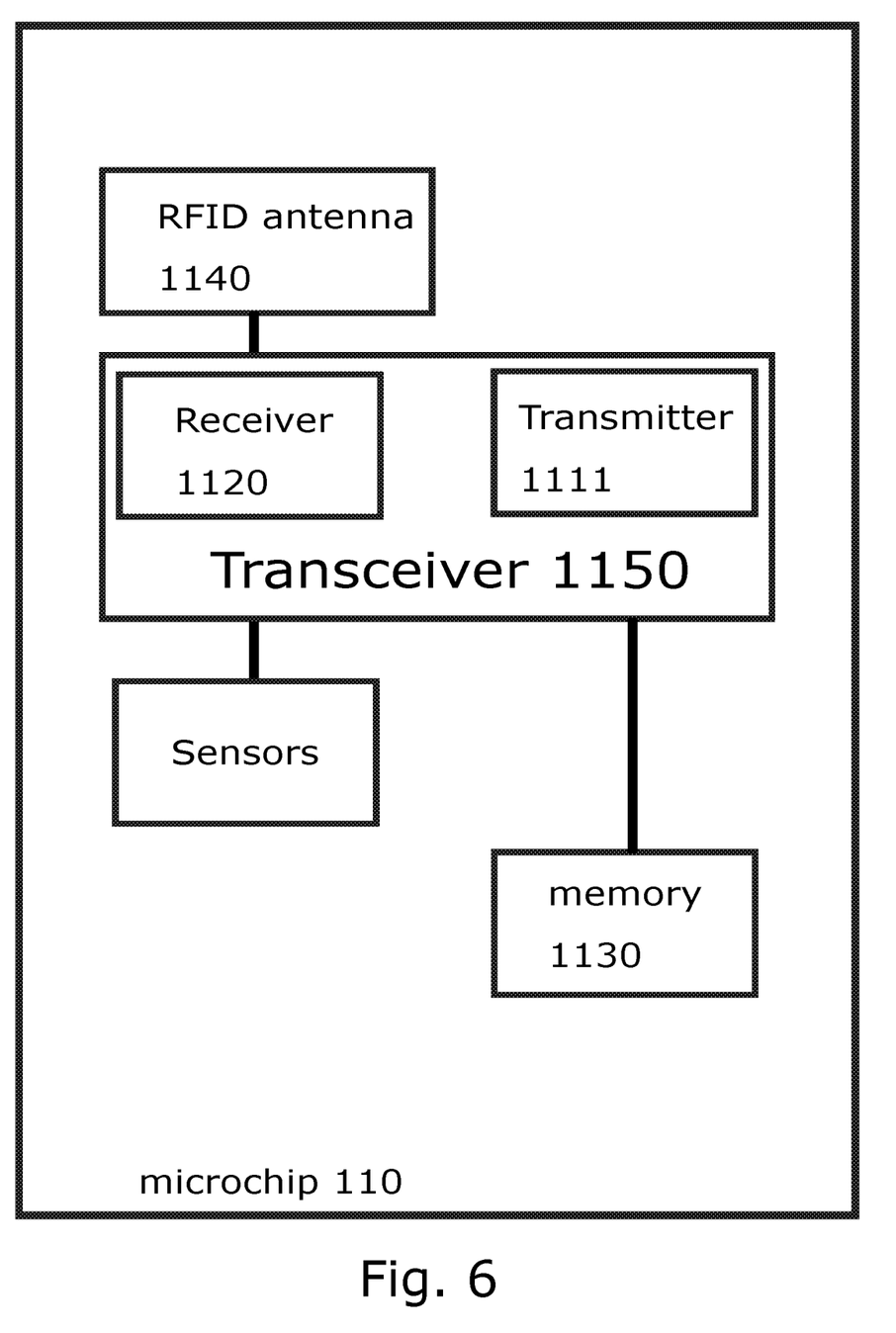
FIG. 6 is a schematic diagram of a microchip denture implant.

Some invention embodiments are kits containing the components used to carry out the methods described above. For instance, in some embodiments, the kit comprises a microchip 110 with a microchip transmitter 1111, a microchip receiver 1120, and a microchip memory 1130 and a dental-prosthetic-grade adhesive. Depending upon the requirements the transmitter and receiver can be combined into a transceiver 1150. In some embodiments the microchip 110 is configured for affixation to a dental-prosthetic 10, the receiver is configured to receive instructions and information from an external reader scanner 130, and the transmitter is configured to send information to an external reader scanner 130.

Other embodiments include kits that, in addition to that described above, include an external reader scanner 130 with a scanner transmitter, a scanner receiver, a scanner memory. This scanner 130 can be an RFID scanner that can send commands and information to the microchip 110 and that can receive information from the microchip 110.

In some embodiments, the microchip 110, which can also have RFID capability including an RFID antenna 1140, responds to interrogation from the scanner 130 to provide or transmit information to the scanner 130. These devices can be configured so that they cannot be interrogated from long distances. Some embodiments do not have the ability to provide location data. This can be for privacy reasons.

Figure 5:
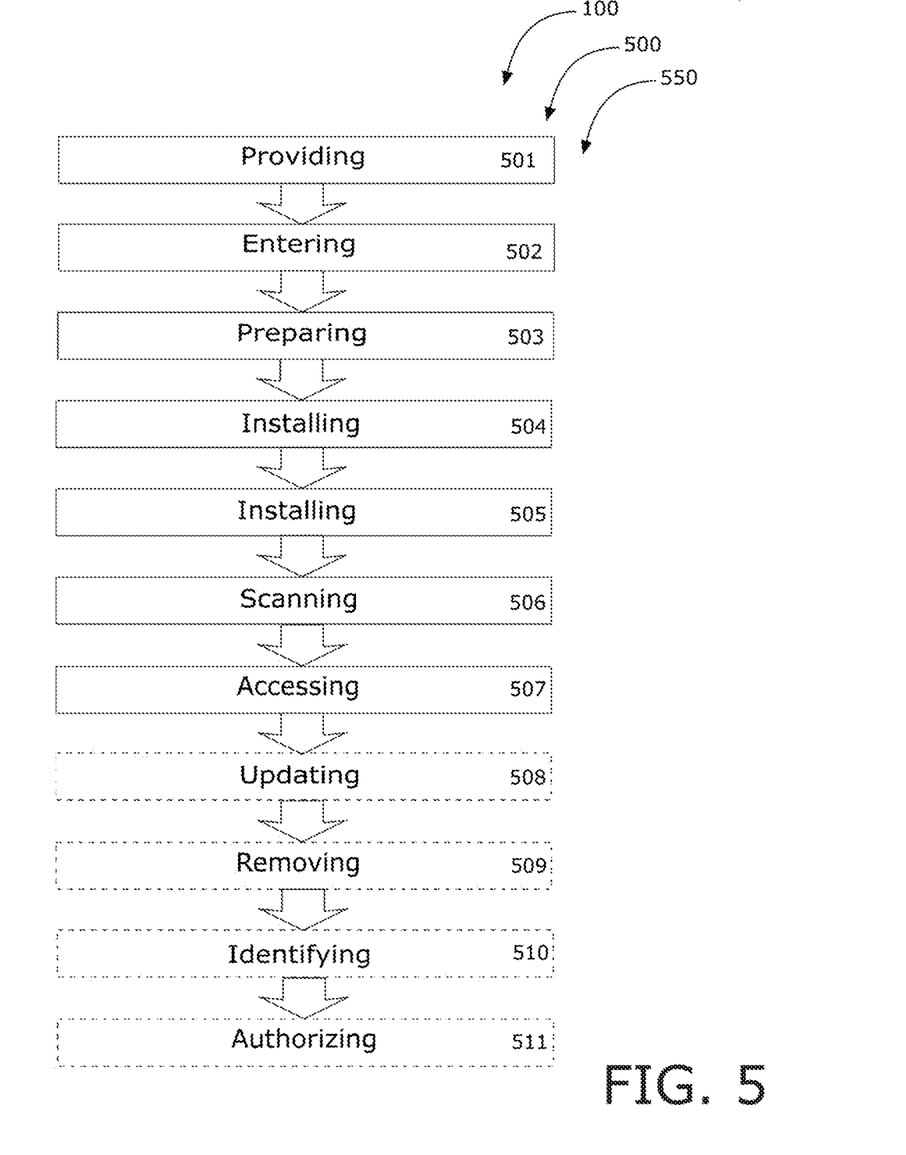
FIG. 5 is a flow diagram illustrating a method of use for the microchip denture implant and reader system, according to an embodiment of the present disclosure.

FIG. 5 is a flow diagram 550 illustrating a method 500 of using the microchip denture implant and reader system 100, according to an embodiment of the present disclosure. As illustrated, a method 500 of using the microchip denture implant and reader system 100 may include step one 501, providing a microchip 110 and an external reader scanner 130; step two 502, entering and programming the microchip 110 with information relating to a user 140; step three 503, preparing a cavity to install the microchip 110 within a dental prosthetic item 10; step four 504, installing the microchip 110 within the dental prosthetic item 10; step five 505, installing the dental prosthetic item 10 in the user's 140 mouth; step six 506, scanning the microchip 110; step seven 507, accessing the information relating to the user 140. The method further comprises the step of step eight 508, updating the information on the microchip 110, step nine 509, removing the dental prosthetic item 10, step ten 510, identifying the user 140, and step eleven 511, authorizing a third-party practitioner (home care, hospital, medical or dental clinic, ambulance, nurse, family, etc.). The dental prosthetic item 10 can be a denture.

Steps eight 508, nine 509, ten 510, and eleven 511 are optional, and all embodiments may not implement them. FIG. 5 uses dotted lines to illustrate optional steps of method 500 are illustrated using dotted lines in FIG. 5 to distinguish them from the other steps of method 500. The steps described in the method can be carried out in many different orders according to user preference. The use of "step of" should not be interpreted as "step for", in the claims herein and is not intended to invoke the provisions of 35 U.S.C. § 112(f). Under appropriate circumstances, considering such issues as design preference, user preferences, marketing preferences, cost, structural requirements, available materials, technological advances, etc., other methods for using the microchip denture implant and reader system 100 (e.g., different step orders within above-mentioned list, elimination or addition of some steps, including or excluding maintenance steps, etc.), are taught herein.

The embodiments of the invention described herein are exemplary, and numerous modifications, variations, and rearrangements can be readily envisioned to achieve substantially equivalent results, all of which are within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is:

1. A denture microchip kit, comprising:
   a microchip including:
      a microchip transmitter;
      a microchip receiver;
      a microchip memory, wherein the microchip is configured for implantation in a milled cavity in a dental prosthetic, wherein the receiver is configured to receive instructions and information from an external reader scanner;
      wherein the microchip transmitter is configured to send information to the external reader scanner;
   the dental prosthetic comprising a milling region having a thickness such that the milled cavity is formed when material is removed therefrom, wherein the milled cavity forms an interior volume sized to receive the microchip;
   wherein the milling region is disposed on a non-tooth portion of the dental prosthetic;
   a dental-prosthetic-grade adhesive adapted to secure the microchip within the milled cavity, wherein the dental-prosthetic-grade adhesive is adapted to seal the milled cavity.

2. The kit of claim 1, further comprising an external reader scanner including:
   a scanner transmitter;
   a scanner receiver;
   scanner memory,
   wherein the scanner transmitter is configured to send commands and information to the microchip receiver and the scanner receiver is configured to receive information from the microchip transmitter.

3. The kit of claim 2, wherein the microchip is configured to respond to instructions by transmitting information from microchip memory.

4. The kit of claim 3, wherein the microchip is configured to respond to instructions by storing information in microchip memory.

5. The kit of claim 1, wherein the microchip has a length and a width of approximately 4 to 6 millimeters.

6. A denture microchip system, comprising:
a dental prosthetic comprising:
a milling region adapted to form a milled cavity when a portion of the milling region is removed therefrom, wherein the milted cavity includes an interior volume that is sized to receive a microchip;
wherein milling region is disposed on a non-tooth portion of the dental prosthetic;
the microchip disposed within the milled cavity of the dental prosthetic, the microchip including:
a transmitter;
a receiver;
a memory;
wherein the receiver is configured to receive instructions and information from an external reader scanner;
wherein the transmitter is configured to send information from the memory to the external reader scanner;
a dental prosthetic grade adhesive disposed within the milled cavity and adapted to close an open end of the milled cavity such that the microchip is secured and concealed within the milled cavity.

7. The denture microchip system of claim 6,
the microchip is configured to respond to instructions by transmitting or storing information from microchip memory.

8. A method of implanting a microchip to a denture prosthetic, comprising:
providing the microchip comprising:
a receiver configured to receive instructions and information from an external reader scanner;
a transmitter configured to send information from a memory to the external reader scanner;
providing the dental prosthetic comprising a milling region disposed on a non-tooth portion thereof;
milling the milling region to form a milled cavity, wherein the milled cavity is dimensioned to receive the microchip.

9. The method of claim 8, further comprising:
applying a dental prosthetic grade adhesive to close an open end of the milled cavity such that the microchip is secured and concealed within the milled cavity.

10. The method of claim 9, further comprising:
installing the microchip within the milled cavity of the dental prosthetic.

11. The method of claim 10, further comprising:
implanting the dental prosthetic in a mouth of a user after the microchip is installed within the milled cavity.

12. The method of claim 11, further comprising:
scanning the microchip with the external reader scanner to receive instructions and information therefrom.

13. The method of claim 12, further comprising:
scanning the microchip with the external reader scanner to send information thereto.

* * * * *